(12) United States Patent (10) Patent No.: US 7,394,254 B2
Rieke et al. (45) Date of Patent: Jul. 1, 2008

(54) MAGNETIC RESONANCE IMAGING HAVING RADIATION COMPATIBLE RADIOFREQUENCY COILS

(75) Inventors: Viola Rieke, Palo Alto, CA (US); Rosemary Kim Butts, Redwood City, CA (US); Arundhuti Ganguly, San Jose, CA (US); Norbert J. Pelc, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/412,419

(22) Filed: Apr. 26, 2006

(65) Prior Publication Data

US 2006/0273795 A1 Dec. 7, 2006

Related U.S. Application Data

(60) Provisional application No. 60/675,528, filed on Apr. 27, 2005.

(51) Int. Cl.
*G01V 3/00* (2006.01)
(52) U.S. Cl. ....................................................... 324/318
(58) Field of Classification Search .................. 324/318
See application file for complete search history.

(56) References Cited

U.S. PATENT DOCUMENTS 4,517,516 A * 5/1985 Hill et al. .................... 324/318
4,939,464 A * 7/1990 Hammer ...................... 324/318
6,448,559 B1 * 9/2002 Saoudi et al. ............... 250/367
6,591,127 B1 * 7/2003 McKinnon ................... 600/411
6,925,319 B2 8/2005 McKinnon ................... 600/407
6,973,162 B2 * 12/2005 Block et al. .................... 378/63
2006/0237652 A1 * 10/2006 Kimchy et al. ......... 250/363.02

OTHER PUBLICATIONS

Raaymakers, B.W., et al., "Integrating a MRI scanner with a radiotherapy accelerator: a new concept of precise on line radiotherapy guidance and treatment monitoring," Department of Radiotherapy and Radiology, University Medical Center Utrecht, Heidelberglaan 100, 3584 CX Utrecht, the Netherlands. Philips Research Hamburg, Germany, Elekta, Crawley, United Kingdom.

* cited by examiner

*Primary Examiner*—Brij B. Shrivastav
*Assistant Examiner*—Megann E Vaughn
(74) *Attorney, Agent, or Firm*—Lumen Patent Firm, Inc.

(57) ABSTRACT

Improved compatibility of MRI with radiation imaging is provided by MRI RF coils having transmissive coil sections. The transmissive coil sections are substantially transparent to the penetrating radiation employed by the radiation imaging system. Thus the transmissive coil sections can be disposed in a field of view of the radiation imaging system without introducing artifacts into the radiation images. Transparency to penetrating radiation can be achieved by substantially including only low atomic number (i.e., Z<29) elements in the transmissive coil sections. Preferably, the transmissive coil sections are fabricated substantially from aluminum.

19 Claims, 4 Drawing Sheets

MAGNETIC RESONANCE IMAGING HAVING RADIATION COMPATIBLE RADIOFREQUENCY COILS

CROSS REFERENCE TO RELATED APPLICATIONS

This application claims the benefit of U.S. provisional application 60/675,528, filed on Apr. 27, 2005, entitled "X-ray Compatible Radiofrequency Coil for Magnetic Resonance Imaging", and hereby incorporated by reference in its entirety.

GOVERNMENT SPONSORSHIP

This invention was made with support from the NIH under contract number R01 EB00198. The government has certain rights in this invention.

FIELD OF THE INVENTION

This invention relates to magnetic resonance imaging.

BACKGROUND

Magnetic resonance imaging (MRI) has been employed for various applications (e.g., medical imaging) for some time. In medicine, combined use of MRI with radiation therapy and with radiation imaging have both been investigated. Such multi-modality systems provide significant advantages compared to single modality systems where a patient may need to be moved or transferred from one system to another system. Such transfers can be difficult and time-consuming, and they can compromise results by complicating image registration.

MRI in combination with a radiotherapy accelerator has been considered by Raaymakers et al. in an article "Integrating a MRI scanner with a radiotherapy accelerator: a new concept of precise on line radiotherapy guidance and treatment monitoring". In this article, an MRI system is described having main magnet coils and gradient coils disposed out of the path of the therapeutic radiation. Although the RF coils of the MRI system are in the radiation path, they do not cause enough absorption heterogeneity to significantly degrade therapy. More specifically, the RF coils in this work had an equivalent Al thickness of about 2.3 cm, which apparently is sufficiently low for the therapy being considered.

Combination of MRI with radiation imaging is more demanding than combination of MRI with radiation therapy. More specifically, if conventional MRI RF coils are disposed in the radiation path of a radiation imaging system, undesirable coil artifacts will tend to be present in the radiation images. For this reason, when MRI is performed in combination with radiation imaging (as opposed to radiation therapy), all coils of the MRI system, including the RF coils, are typically disposed out of the radiation path. For example, U.S. Pat. No. 6,925,319 considers a split magnet MRI system having all MRI coils disposed out of the radiation path of an X-ray system.

Unfortunately, MRI performance can be undesirably degraded by a requirement to place the MRI RF coils outside the field of view of a radiation imaging system. For example, surface RF coils are often placed directly on a subject being imaged for maximum MRI image quality. Such a surface coil is in the field of view of any radiation imaging system that is directed to the same part of the subject as the MRI system, which is the situation of greatest practical interest. Thus conventional combined MRI and radiation imaging can oblige an undesirable choice among accepting reduced MRI image quality (by placing the RF coils out of the radiation system field of view), accepting RF coil artifacts in the radiation images (by placing the RF coils in the radiation system field of view), or moving the MRI RF coils to one position for MRI imaging and to another position (out of the field of view) for radiation imaging.

Accordingly, it would be an advance in the art to provide radiation imaging compatible MRI RF coils. It would also be an advance in the art to provide radiation imaging compatible MRI systems, either separately or in combination with a radiation imaging system.

SUMMARY

Improved compatibility of MRI with radiation imaging is provided by MRI RF coils having transmissive coil sections. The transmissive coil sections are substantially transparent to the penetrating radiation employed by the radiation imaging system. Thus the transmissive coil sections can be disposed in a field of view of the radiation imaging system without introducing artifacts into the radiation images. Transparency to penetrating radiation can be achieved by substantially including only low atomic number (i.e., Z<29) elements in the transmissive coil sections. Preferably, the transmissive coil sections are fabricated substantially from aluminum.

Embodiments of the invention include radiation imaging compatible MRI RF coils, MRI systems including radiation compatible MRI RF coils, and multi-modality imaging systems including a radiation imaging subsystem and an MRI subsystem having RF coils compatible with the radiation imaging subsystem.

DETAILED DESCRIPTION

Figure 1:
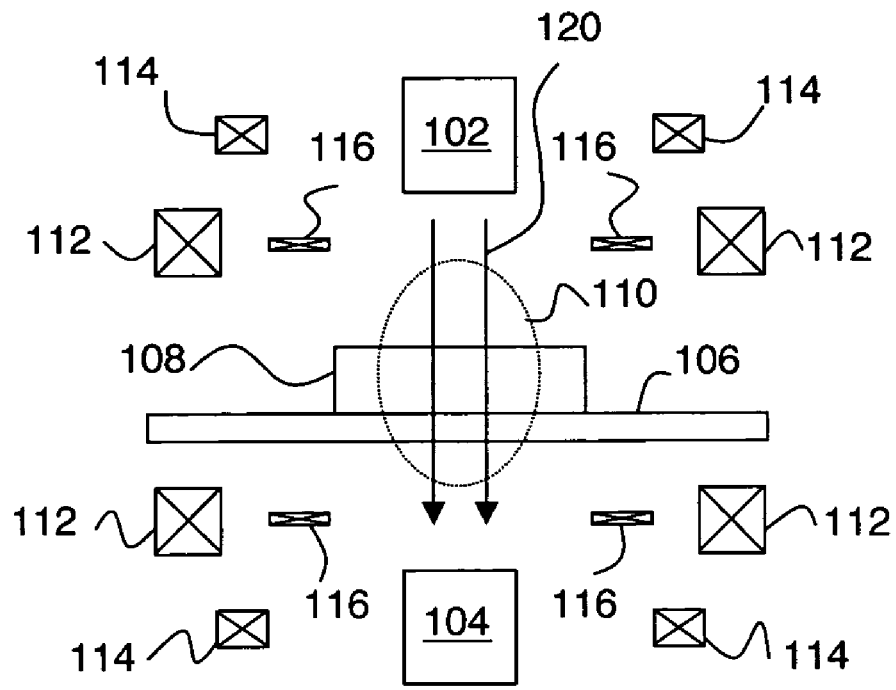
FIG. 1 shows a prior art multi-modality imaging system.

FIG. 1 shows a conventional multi-modality imaging system. A radiation imaging subsystem including a source 102 and a detector 104 passes penetrating radiation 120 through a sample 108 disposed on a table 106. For medical imaging applications, sample 108 is typically a human patient. The system of FIG. 1 also includes an MRI imaging subsystem having main magnetic coils 112, gradient coils 114 and RF coils 116. The configuration shown in FIG. 1 is a split magnet configuration (as in U.S. Pat. No. 6,925,319) having the MRI coils disposed out of a field of view 110 of the radiation imaging subsystem. Since the MRI coils in this system are not in field of view 110, coil artifacts do not appear in the images provided by the radiation imaging system. However, the resulting coil locations can be sub-optimal for MRI performance, undesirably reducing MRI image quality.

Figure 2:
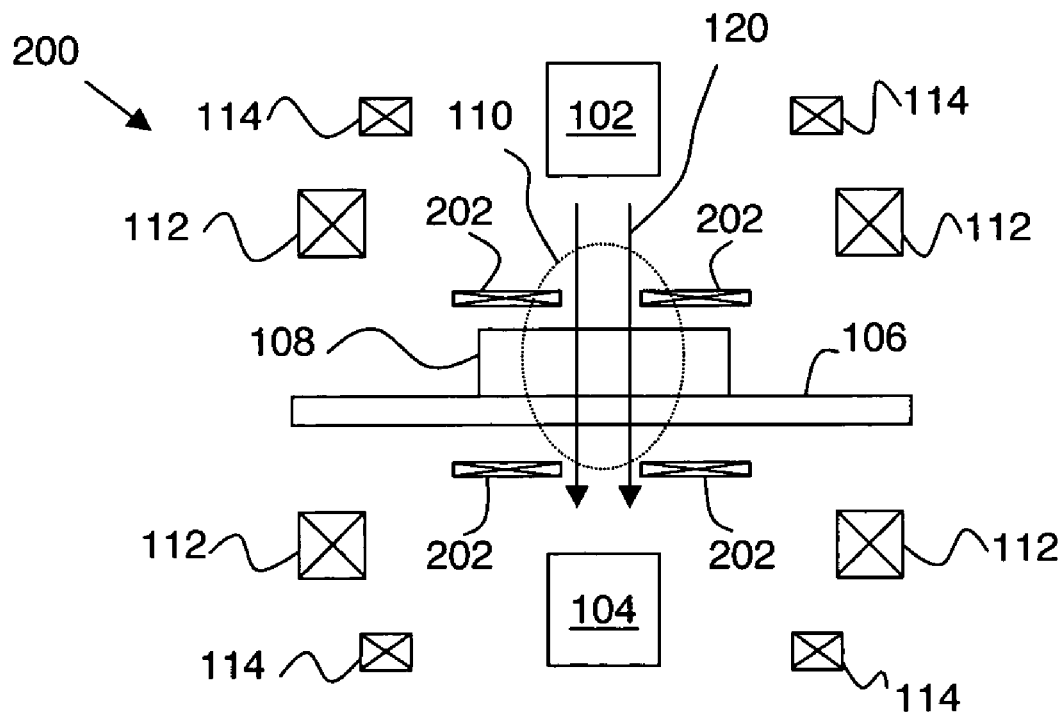
FIG. 2 shows a multi-modality imaging system according to an embodiment of the invention.

FIG. 2 shows a multi-modality imaging system according to an embodiment of the invention. Here radiation compatible RF coils 202 are disposed such that one or more of RF coils 202 extend into the radiation imaging field of view 110. More specifically, each such RF coil includes a transmissive RF coil section, and it is the transmissive section of each coil that extends into field of view 110. The transmissive RF coil section can be part of the RF coil, or it can include the entire RF coil. The transmissive RF coil section of RF coils 202 are substantially transparent to penetrating radiation 120. Since RF coils 202 do not interfere with radiation imaging, MRI images and radiation images can be obtained simultaneously or nearly simultaneously. This capability is a significant advantage of the invention compared to systems where the MRI RF coils are moved out of the field of view when radiation images are taken. The system of FIG. 2 could also include conventional RF coils (not shown) in addition to the radiation compatible RF coils. For example, it could have a transmit body coil outside the field of view 110 of the radiation imaging system.

Special measures are required to provide MRI RF coils having transmissive sections as described above. Since the linear attenuation of diagnostic X-rays varies approximately as the fourth power of atomic number (Z), it is preferred for the transmissive coil sections to substantially include only low-Z (Z<29) elements. In particular, we have found that use of conventional RF MRI coils fabricated of Cu (Z=29) leads to coil artifacts in X-ray images, while similar RF coils fabricated of Al (Z=13) do not lead to X-ray image artifacts. Thus it is preferred for the transmissive RF coil sections to include no copper wires or traces. It is also preferred for the transmissive RF coil sections to be substantially fabricated of aluminum. Finally, it is preferred for the transmissive RF coil sections to include no soldered electrical connections, since such connections typically include high-Z elements (e.g., tin, zinc) in the solder. The AC conductivity of Al (i.e., including the skin effect) is about 80% of the AC conductivity of Cu. Thus Al is nearly as good a conductor as Cu. This 80% ratio is independent of frequency, since the decrease in AC conductivity as RF frequency increases has the same functional form in all metals.

The language "substantially include only low-Z elements" includes cases where the transmissive coil sections are mainly fabricated of low Z elements, but also include a small fraction of high Z elements (e.g., as a small component of an alloy, trace contamination, etc.). As long as the radiation attenuation provided by any such high-Z elements is negligible, their inclusion in the transmissive coil sections is harmless.

MRI coils are typically placed within a protective enclosure during use. Parts of the enclosure that are within the field of view of the radiation imaging system preferably provide low and uniform attenuation of the radiation, in combination with mechanical strength, flexibility and durability. A plastic layer in combination with rubber foam has served as a suitable MRI RF coil enclosure in our experiments. In cases where the transmissive RF coil sections include aluminum, it is advisable for the coil enclosure to provide sufficient mechanical support to protect any Al solder joints that may be present, since such joints are relatively brittle compared to conventional copper soldered joints. Further details relating to transmissive RF coils are provided in the following examples.

Figure 3:
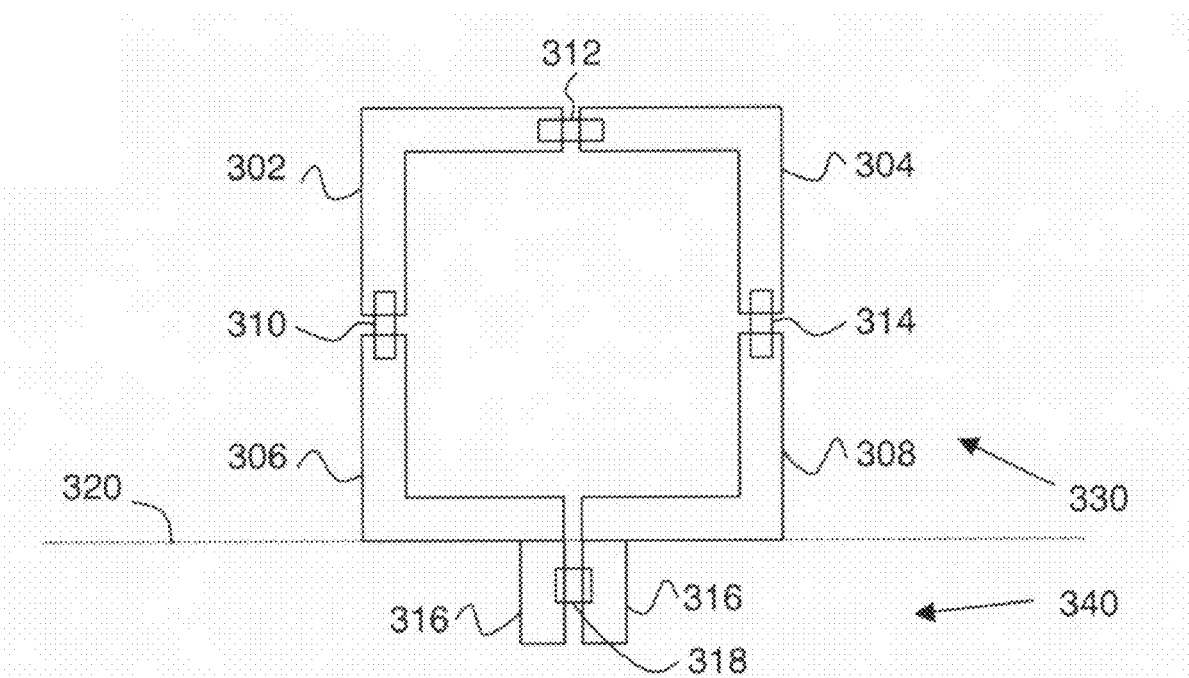
FIG. 3 shows an MRI RF coil according to an embodiment of the invention.

FIG. 3 shows an example of an MRI RF coil having a transmissive RF coil section 330 capable of being placed in the field of view of a radiation imaging system. The RF coil of FIG. 3 is a rectangular 16 cm surface coil including conductors 302, 304, 306, and 308 and capacitors formed by the overlap of segments 310, 312 and 314 with the conductors. This arrangement of capacitors and conductors was fabricated from laminated Aluminum shim stock (MSN Industrial Supply Co., Melville, N.Y., USA) having 50 μm thick Al layers separated by 50 μm of an unspecified dielectric. The composition of the dielectric is not critical for practicing the invention, although mechanically sturdy dielectrics having low electrical loss at the relevant RF frequencies are preferred. One of the Al layers of the shim stock is patterned into conductors 302, 304, 306, and 308, and the other Al layer is patterned into segments 310, 312, and 314, thereby forming an arrangements of conductors and capacitors suitable for use as an MRI RF coil.

The coil of FIG. 3 also includes Cu layers 316 and an input capacitor 318, which can be placed outside the field of view of the radiation imaging system (i.e., in non-transmissive coil section 340). Dotted line 320 separates the transmissive RF coil section 330 from the non-transmissive coil section 340. Non-transmissive coil section 340 can also include other conventional MRI RF coil components, such as leads, a detuning circuit for receive-only RF coils, baluns and cable connections. Since non-transmissive coil section 340 is not disposed in the field of view of the radiation imaging system, there are no restrictions on the chemical elements which can be included in non-transmissive coil section 340.

Figure 4:
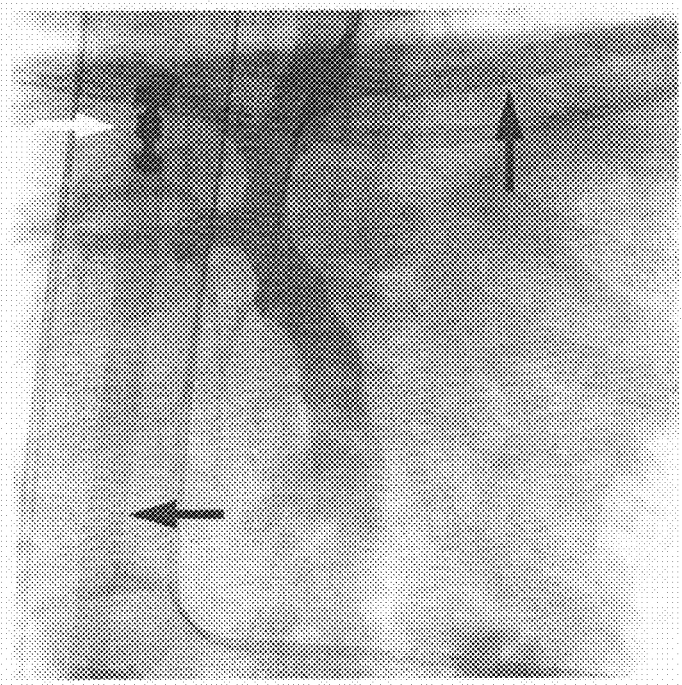
FIG. 4 is an X-ray image showing artifacts from a conventional prior art MRI RF coil in the field of view.

FIG. 4 shows an X-ray image taken with a conventional MRI RF coil in the field of view. Here the coil conductors (black arrows), capacitor (white arrow), and coil housing are visible in the image, undesirably obstructing anatomic features.

Figure 5:
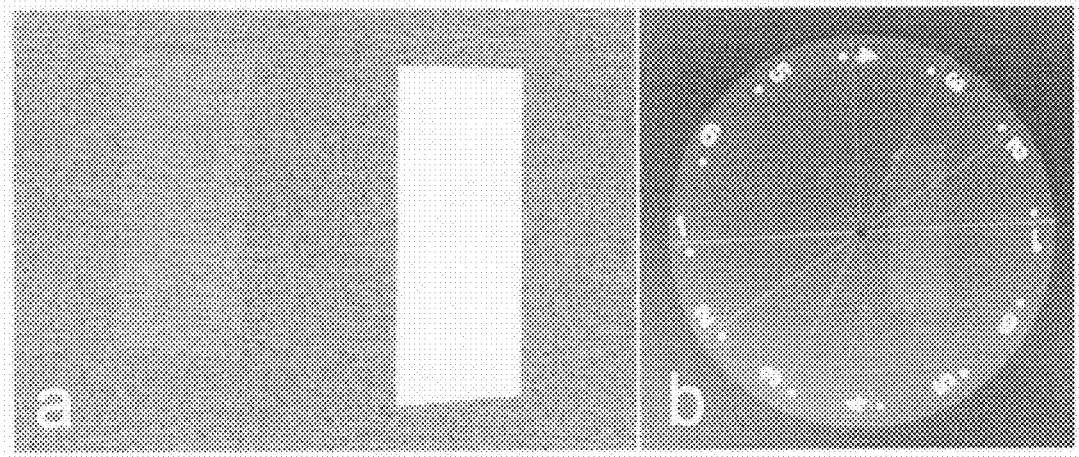
FIGS. 5a-b are X-ray images of Cu and Al samples.

FIG. 5a shows X-ray attenuation of a 50.8 μm thick Al strip (left) and a 35.5 μm thick Cu strip (right) at 50 kVp and 2 mm Al filtration. The measured attenuation for the Cu and Al strips is 22% and 1.1% respectively. For higher tube voltages and filtrations, the attenuation of both strips decreases, but the attenuation of the Al strip remains significantly below that of the Cu strip. FIG. 5b shows X-ray attenuation of the two strips placed on top of a 20 cm Lucite® layer containing a guide wire phantom. The Al strip is not detectable, while the Cu strip remains visible in the image with a contrast of 5%.

Figure 6:
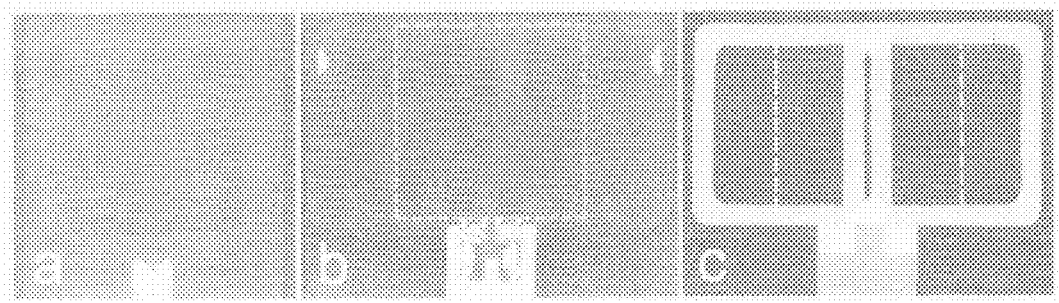
FIGS. 6a-b are X-ray images of MRI RF coils according to embodiments of the invention.
FIG. 6c is an X-ray image of a conventional MRI RF coil.

FIG. 6a shows an X-ray image of the surface coil of FIG. 3. The input capacitors and some elements of the detuning circuit are visible at the edge of the image. FIG. 6b shows an X-ray image of two elements of a 4 element phased array (PA) MRI RF coil according to the invention. This abdominal coil was made transmissive by using Al loops as the array elements, and by moving the loop capacitors to locations outside the X-ray field of view (e.g., in the detuning circuit and/or to the sides of the field of view). This allows the use of conventional, discrete capacitors (as compared to the strip capacitors in the coil of FIGS. 3 and 6a). The field of view of the operational radiation imaging system is shown with a dotted line, showing that the loop capacitors are outside the field of view. For comparison, FIG. 6c shows an X-ray image of a conventional Cu phased array RF coil. This coil has the same design as the coil of FIG. 6b, except that the array loops are made of 35.5 μm thick Cu foil. The conventional PA coil of FIG. 6c clearly leads to much larger image artifacts in the field of view than the embodiment of FIG. 6b.

The measured unloaded/loaded Q factor ratio of the individual coils of the X-ray compatible coil of FIG. 6b is about 270/40. For comparison, the conventional coil of FIG. 6c has a Q factor ratio of about 185/50, and the X-ray compatible surface coil of FIG. 3 has a Q factor ratio of about 50/24. The X-ray compatible coil of FIG. 6b has a sufficiently high Q that MRI signal noise is dominated by sample noise. However, the relatively low Q of the X-ray compatible surface coil of FIG. 3 means that the coil itself undesirably contributes to MRI signal noise. In this experimental work, the low Q factor was found to be caused by high electrical loss in the dielectric separating the Al layers. Thus, as indicated above, it is preferred for the dielectric layer in the embodiment of FIG. 3 to have low electrical loss.

Figure 7:
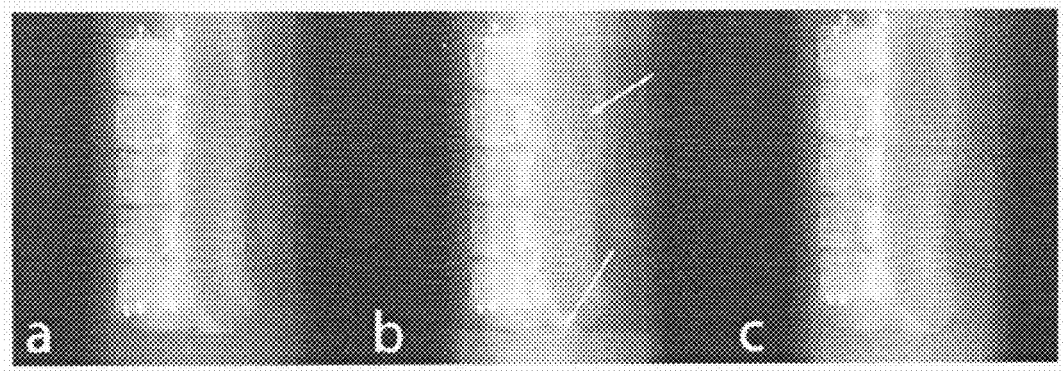
FIG. 7a is an X-ray image of a porcine spine phantom with no MRI RF coil present in the field of view.
FIG. 7b is an X-ray image of a porcine spine phantom with a conventional MRI RF coil present in the field of view.
FIG. 7c is an X-ray image of a porcine spine phantom with a radiation compatible MRI RF coil according to an embodiment of the invention present in the field of view.

FIG. 7a is an X-ray image of a porcine spine phantom with no MRI RF coil present in the field of view. FIG. 7b is an X-ray image of a porcine spine phantom with the conventional MRI RF coil of FIG. 6c present in the field of view. Image artifacts from the MRI coil are shown by white arrows. FIG. 7c is an X-ray image of a porcine spine phantom with the radiation compatible PA coil of FIG. 6b present in the field of view. No coil artifacts are seen on FIG. 7c.

Figure 8:
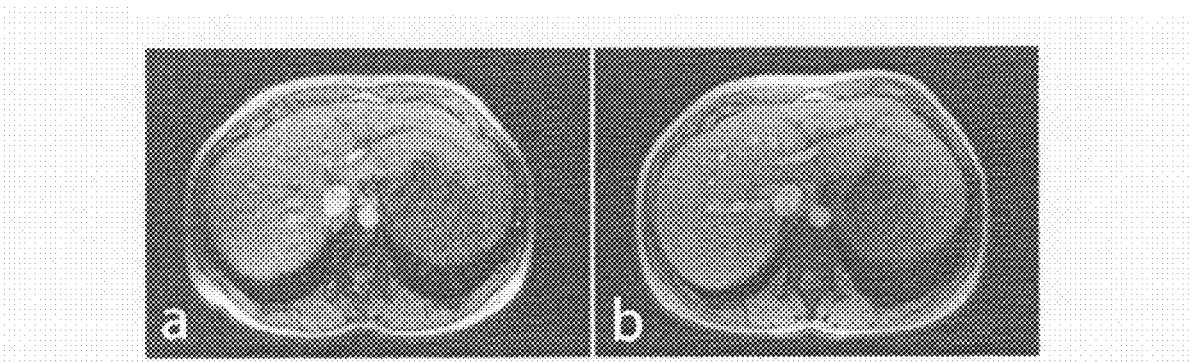
FIG. 8a is an abdominal MRI image obtained with a conventional single channel receive RF coil.
FIG. 8b is an abdominal MRI image obtained with an X-ray compatible phased-array RF coil according to an embodiment of the invention.

FIG. 8a is an abdominal MRI image obtained with a conventional single channel receive RF coil of a type commonly used in combination with X-ray imaging (same type as in FIG. 4). FIG. 8b is an abdominal MRI image obtained with an X-ray compatible phased-array RF coil according to an embodiment of the invention. The result of FIG. 8a is a typical result for the trade-off between radiation image artifacts and MR image quality. This coil type has lower MR image quality than other coil types, but creates only some radiation imaging artifacts (as seen in FIG. 4). Other coil types that provide better MR image quality (e.g. phased-array coils), cannot be used due to their more severe radiation imaging artifacts. Use of an X-ray compatible RF coil allows the choice of an RF coil type that provides the highest MR image quality, without constraints on the placement in the X-ray field of view, thereby improving MRI performance. More specifically, the improvement in MRI signal to noise ratio (SNR) with the X-ray compatible coil of FIG. 8b is 60% compared to the SNR provided by the coil of FIG. 8a.

Embodiments of the invention have been employed to perform multi-modality imaging during interventional procedures. In the following two examples, the X-ray compatible PA RF coil of FIG. 6b was employed.

Figure 9:
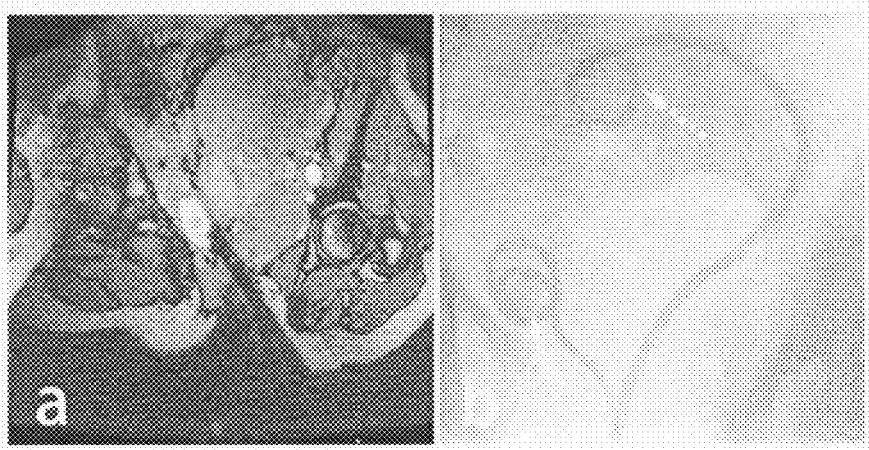
FIGS. 9a-b are combined MRI and X-ray images provided by an embodiment of the invention.

FIGS. 9a-b are MRI and X-ray images provided by an embodiment of the invention, acquired in a combined X-ray/MR imaging system. FIG. 9a shows an MR image obtained during percutaneous vaginal reconstruction. MR imaging was employed to guide transperineal needle puncture into the upper vagina. MR imaging included a fast gradient echo sequence with TR/TE=30/7.5 ms, flip angle=60°, BW=±15.6 kHz, FOV=30 cm, matrix size=256×128, and slice thickness=5 mm. Catheter placement into the upper vagina (solid arrow) and the left fallopian tube (dotted arrow) was visualized in an X-ray image, as seen in FIG. 9b. The X-ray image of FIG. 9b does not show RF MRI coil artifacts.

Figure 10:
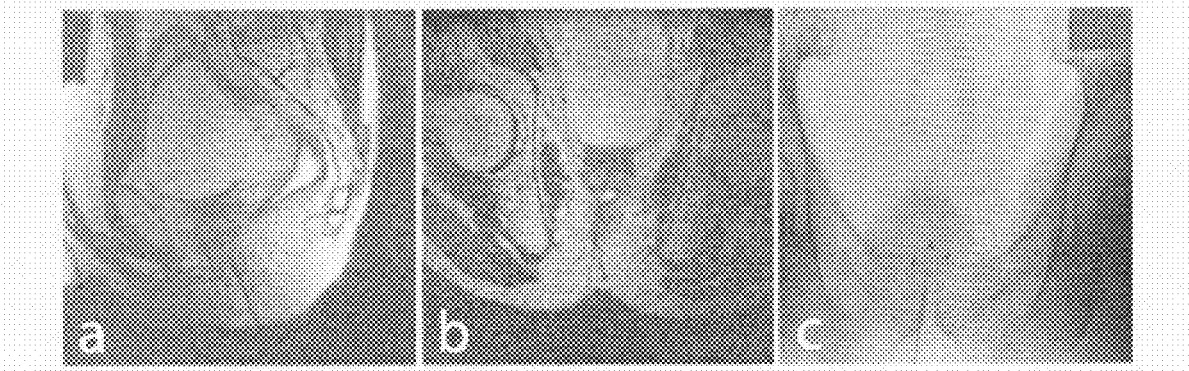
FIGS. 10a-c are combined MRI and X-ray images provided by an embodiment of the invention.

FIGS. 10a-c are MRI and X-ray images provided by an embodiment of the invention, acquired in a combined X-ray/MR imaging system. FIGS. 10a and 10b are MR images (sagittal and coronal, respectively) obtained during prostate seed placement. MR imaging included a $T_2$-weighted fast spin echo sequence with TR/TE=3000/140 ms, BW=±12.5 kHz, echo train length=12, FOV=30 cm, matrix size=256×160, and slice thickness=5 mm. FIG. 10c shows a corresponding X-ray image. Again, no MRI coil artifacts are visible in the X-ray image.

Although the preceding description and examples relate mainly to X-ray imaging, the invention is applicable to radiation imaging with any kind of penetrating electromagnetic radiation (i.e., X-rays and/or gamma rays). Suitable radiation imaging subsystems include, but are not limited to: X-ray imaging systems, positron emission tomography systems, single photon emission computed tomography systems, X-ray computed tomography systems, and nuclear medical imaging systems.

The preceding examples relate to multi-modality imaging including radiation imaging in the A/P direction. The principles of the invention are also applicable in multi-modality systems where the radiation projection angle is arbitrary (e.g., C-arm systems).

The invention claimed is:

1. An MRI-radiation multi-modality imaging system comprising:
   a radiation imaging subsystem for generating a radiation image of a subject using penetrating electromagnetic radiation; and
   a magnetic resonance imaging (MRI) subsystem for generating an MRI image of the subject, wherein the MRI subsystem includes one or more radio-frequency (RF) coils;
   wherein a field of view of the radiation imaging subsystem includes transmissive RF coil sections of each of the one or more RF coils;
   wherein the transmissive RF coil sections of said one or more RF coils are substantially transparent to the penetrating radiation.

2. The system of claim 1, wherein said radiation imaging subsystem comprises an imaging system selected from the group consisting of: X-ray imaging systems, positron emission tomography systems, single photon emission computed tomography systems, X-ray computed tomography systems, and nuclear medical imaging systems.

3. The system of claim 1, wherein said penetrating electromagnetic radiation comprises X-rays or gamma rays.

4. The system of claim 1, wherein said transmissive RF coil sections do not include any copper wires or traces.

5. The system of claim 1, wherein said transmissive RF coil sections are substantially fabricated of aluminum.

6. The system of claim 1, wherein said transmissive RF coil sections substantially include only chemical elements having atomic number less than 29.

7. The system of claim 1, wherein said transmissive RF coil sections include no soldered electrical connections.

8. A magnetic resonance imaging system comprising:
   a main magnet subsystem;
   a gradient coil subsystem; and
   a radio-frequency (RF) coil subsystem, wherein the RF coil subsystem includes one or more RF coils;
   wherein at least one such RF coil includes a transmissive RF coil section adapted to be placed in a field of view of a radiation imaging system;
   wherein at least one of the transmissive RF coil sections is substantially transparent to a penetrating electromagnetic radiation used in radiation imaging.

9. The system of claim 8, wherein said transmissive RF coil sections do not include any copper wires or traces.

10. The system of claim 8, wherein said transmissive RF coil sections are substantially fabricated of aluminum.

11. The system of claim 8, wherein said transmissive RF coil sections are substantially fabricated of materials including only chemical elements having atomic number less than 29.

12. The system of claim 8, wherein said transmissive RF coil sections include no soldered electrical connections.

13. An MRI-radiation multi-modality imaging method comprising:

provising a radiation image of a subject with a radiation imaging subsystem using penetrating electromagnetic radiation; and providing a magnetic resonance imaging (MRI) image of the subject with an MRI subsystem including one or more radio-frequency (RF) coils;

wherein a field of view of the radiation imaging subsystem includes transmissive coil sections of each of the one or more RF coils;

wherein said transmissive coil sections are substantially transparent to the penetrating electromagnetic radiation.

14. The method of claim 13, wherein said radiation image and said MRI image are acquired substantially simultaneously.

15. A radio-frequency (RF) coil for use in a magnetic resonance imaging (MRI) system, the RF coil comprising:

an arrangement of conductors and capacitors suitable for use as an RF coil of an MRI system;

wherein some or all of the conductors and capacitors are included within a transmissive RF coil section;

wherein the transmissive RF coil section is capable of being placed in a field of view of a radiation imaging system employing penetrating electromagnetic radiation;

wherein the transmissive RF coil section is substantially transparent to the penetrating electromagnetic radiation.

16. The RF coil of claim 15, wherein said transmissive RF coil section does not include any copper wires or traces.

17. The RF coil of claim 15, wherein said transmissive RF coil section is substantially fabricated of aluminum.

18. The RF coil of claim 15, wherein said transmissive RF coil section substantially includes only chemical elements having atomic number less than 29.

19. The RF coil of claim 15, wherein said transmissive RF coil section includes no soldered electrical connections.

* * * * *